United States Patent [19]

Kramer

[11] 4,098,112

[45] Jul. 4, 1978

[54] STEAM TURBINE EXPANSION JOINT WITH PROBE FOR MONITORING MOLTEN CAUSTICS

[75] Inventor: Leslie D. Kramer, Wilmington, Del.

[73] Assignee: Westinghouse Electric Corp., Pittsburgh, Pa.

[21] Appl. No.: 776,327

[22] Filed: Mar. 10, 1977

[51] Int. Cl.² .................. G01R 27/02; G08B 21/00
[52] U.S. Cl. ........................... 73/28; 324/65 CR; 340/620
[58] Field of Search ............ 73/28, 86, 304 R; 324/65 CR, 71 E; 340/244 C; 200/61.05, 61.04, 61.2; 116/109, 118 R, 118 A

[56] References Cited

U.S. PATENT DOCUMENTS

| | | | |
|---|---|---|---|
| 3,382,493 | 5/1968 | Loper, Jr. et al. | 340/244 C |
| 3,582,930 | 6/1971 | Wiley | 340/244 C |
| 3,996,124 | 12/1976 | Eaton et al. | 324/65 CR X |
| 4,011,553 | 3/1977 | Barri | 340/244 C X |

Primary Examiner—Richard C. Queisser
Assistant Examiner—Joseph W. Roskos
Attorney, Agent, or Firm—J. W. Keen

[57] ABSTRACT

The first ends of two electrical probes extend through and are spatially separated on the interior of a steam turbine's crossover conduit expansion joint. The external, second ends of the electrical probes are connected to an electrical potential source in such manner as to cause the probes to be electrically opposite in charge. A current measuring device is electrically connected to the electrical probes and indicates electrical current flowing therethrough, which, in turn, provides a measure of the quantity of electrically conductive molten caustic which accumulates between the probes' first ends. The probes' first ends are placed in the expansion joint region where molten caustic is most likely to collect, allowing early detection of corrosive caustic during steam turbine operation. A non-corrosive baffle, disposed upstream from the probes' first ends, provides a shield for the first ends from steam born solid particles of low electrical conductivity.

5 Claims, 4 Drawing Figures

STEAM TURBINE EXPANSION JOINT WITH PROBE FOR MONITORING MOLTEN CAUSTICS

BACKGROUND OF THE INVENTION

This invention relates to steam turbine crossover conduit expansion joints and more particularly to a molten caustic detector which can be installed in the steam turbine crossover conduit expansion joint.

Current fossil fuel power plants have crossover conduit expansion joint designs that generally utilize two-ply bellows with various numbers and sizes of convolutions. In the presence of molten sodium hydroxide or certain sodium hydroxide salt mixtures brought into the turbine by improper boiler feedwater addictive control, caustic stress corrosion cracking can cause the bellows' inner ply to fail. Present practice for detecting expansion joint failure is to monitor the pressure between the two plies in the bellows with a change in the pressure indicating an inner ply leak. Unfortunately, however, by the time such pressure change indication occurs, the bellows must be replaced since outer ply failure is then imminent. More importantly, failure of the bellows' inner ply is an indication of the extent of caustic corrodent which has passed through the turbine and which can cause even more serious failures inside the turbine resulting in long and expensive forced outages for the turbine generator.

It has been found that the cracking mechanism of the expansion joint bellows results from the molten phase of sodium hydroxide collecting in convolutions along the horizontal bottom or "six o'clock" position of the bellows as installed. Thus, to detect the molten phase of sodium hyroxide the optimum detector position would be in the previously mentioned "six o'clock" region. Typical temperature conditions of 550 to 750° F and approximately 200 psi pressure in the crossover conduit expansion joint favor sodium hydroxide or sodium hydroxide salt eutectics as the most common molten steam born contaminant. It has been found that under these temperature and pressure conditions the molten sodium hydroxide or sodium hydroxide salt eutectics are good electrical conductors with their conductivity rising with their temperature.

From past experience and operating problems encountered during such experience, early detection of the presence of such caustics is highly desirable to avoid damage not only to the crossover conduit expansion joint, but also to other critical, susceptible turbine elements. It is also desirable that caustic detection occur before the crossover conduit expansion joint has failed to an extent not easily reparable. A third objective of such a caustic detector would be to have the ability to monitor several areas of the turbine system and respond to caustic exposure thereto.

SUMMARY OF THE INVENTION

In general, a steam turbine system caustic detector when made in accordance with this invention, comprises a pair of electrical probes which extend through a steam turbine crossover conduit expansion joint and are spatially separated on the interior thereof with those electrical probes each having their other ends receiving an electrical potential difference with a current measuring device being appropriately disposed to indicate the level of current passing through the electrical probes. By disposing the pair of spatially separated electrical probes on the horizontal bottom of the expansion joint, molten, conductive caustics can collect therebetween and eventually cause the spatially separated electrical probes to be electrically connected, completing a circuit and causing a current indication to register on the current measuring device. Such positioning of the spatially separated electrical probes allow early detection of molten caustic thus preventing failure of the crossover conduit expansion joint. In addition, shielding the spatially separated electrical probes by disposing a non-corrodible baffle upstream of such probes allows detection of only molten caustics since other steam-born contaminants are solid at typical crossover conduit expansion joint temperatures and are thus deflected by the upstream baffle.

BRIEF DESCRIPTION OF THE DRAWINGS

The objects and advantages of this invention will become more apparent from reading the following detailed description in connection with the accompanying drawings in which corresponding reference characters indicate corresponding portions throughout the drawings and in which.

DESCRIPTION OF THE PREFERRED EMBODIMENT

Figure 1:
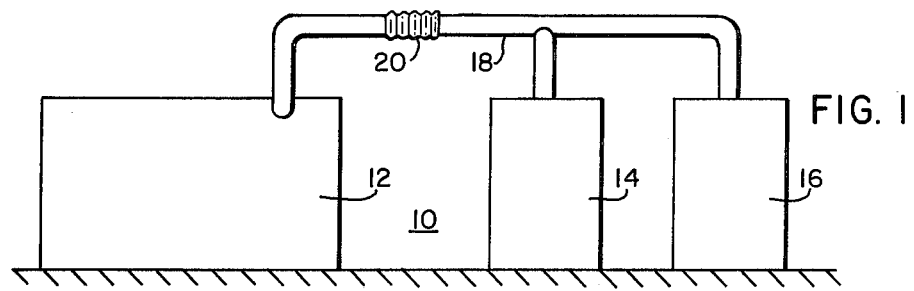
FIG. 1 is an elevation view of a steam turbine having multiple sections thereto which are connected by crossover pipes with expansion joints disposed therein.
Figure 2:
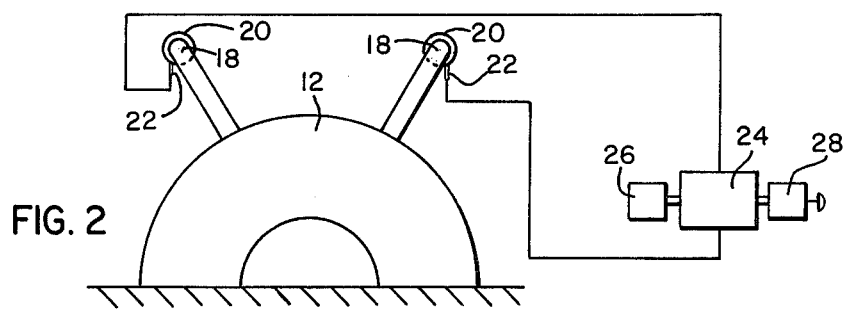
FIG. 2 is an end view of the turbine illustrated in FIG. 1 with the caustic detector shown disposed in the crossover pipes' expansion joints.

Referring now to the drawings in detail, FIGS. 1 and 2 show turbine 10 having multiple housings 12, 14 and 16 fluidly connected by crossover conduits 18. Crossover conduits 18 have expansion joints 20 disposed therein to allow thermal expansion of crossover conduits 18 without creating abnormally large thermal stresses therein due to the stationary locations of the pipes' terminating portions into the turbine sections. In addition, FIG. 2 shows the end view of turbine section 12 and illustrates the relative positioning in expansion joint 20 that caustic detector probes 22 assume therein. Caustic detector probes 22 are connected with a multi-channel recorder 24 which has a wheatstone bridge 26 and suitable alarm 28 connected thereto. Probes 22 are electrically connected to multi-channel recorder 24 by means of an insulated compensating wire with the insulation being a ceramic such as alumina or other material having good thermal shock resistance and mechanical properties.

Figure 3:
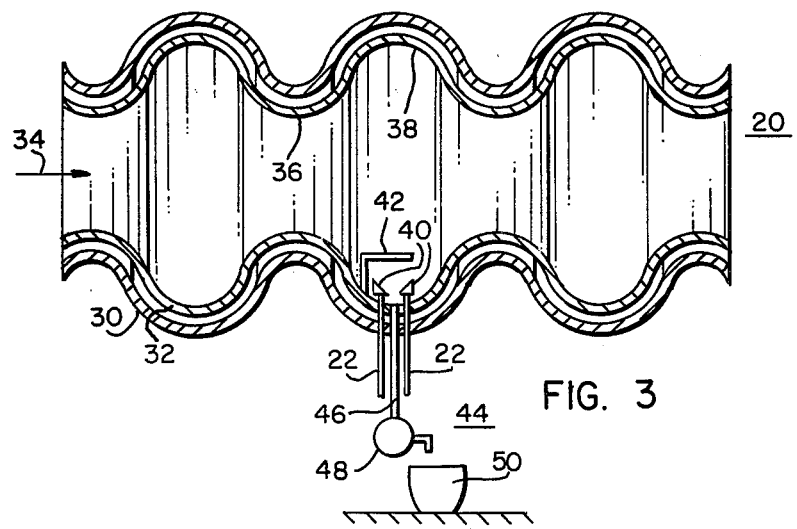
FIG. 3 is a sectional view of the caustic detector disposed in the crossover expansion joint.

FIG. 3 shows a cross-sectional view of the expansion joint 20 and how electrical probes 22 are arranged and shielded therein. Expansion joint 20 is seen to have a bellow-like wall which has an outer ply 30 and an inner ply 32 which are radially separated by appropriate air space or vacuum enclosure. The normal steam flow direction through expansion joint 20 is indicated by arrow 34. The bellow-like wall of expansion joint 20 is made up of plies 30 and 32 which are arranged in inward and outward protruding convolutions disposed circumferentially around the steam flow path and exemplified by numbers 36 and 38 respectively. Electrical probes 22 are shown in FIGS. 2 and 3 as protruding through wall plys 30 and 32 where they form an outward protruding convolution 38 at that outward protruding convolution's lowest circumferential position around the expansion joint 20.

Electrical probes 22 are shown terminating on the interior of expansion joint 20 with each probe having an electrode 40 attached thereto which is of triangular shape so as to prevent retention of molten caustic after the caustic level drops in the outward protruding convolution. Shield baffle 42 is constructed of nickel, is disposed upstream from electrodes 40, and is arranged to shield them from steam-born solid particles which are normally distributed evenly on the interior of the expansion joint 20. By shielding such solid contaminants from exposure to electrodes 40, alarm indications from electrical probes 22 will only result from liquid contaminants in the steam which deposit on inner ply 32 and drain into the circumferentially lowest portion of expansion joint 20 causing outward protruding convolutions 38 which are situated in the "six o'clock" position to collect fluid therein. Temperature and pressure conditions of the steam in crossover conduit expansion joints favor molten phases of very few materials. The primary molten phases which occur therein are caustic solutions of sodium hydroxide and sodium hydroxide salt eutectic combinations such as sodium carbonate, sodium phosphate, and sodium sulphate. Such molten caustic solutions exhibit substantial conductivity and that conductivity is utilized to electrically connect electrodes 40 causing an alarm indication and yielding a measure of the quantity of conductive caustic that has accumulated.

A blowdown scheme 44 is also illustrated in FIG. 3. Conduit 46, as shown, extends through inner and outer plies 32 and 30 terminating on the interior of expansion joint 20. Conduit 46 is arranged so that when valve 48 is opened, any foreign substances accumulated between electrodes 40, including the previously mentioned conductive caustic, can be drained into a sample container 50. Thus, after the presence of corrosive caustic has been detected, valve 48 may be operated to clear the electrodes of molten residue accumulated there during the steam chemistry excursion. Collecting the blown down foreign substances in the sample container 50 allows them to be chemically analyzed and provides a system diagnostic by facilitating the determination of the cause for the caustic contamination of the steam.

Figure 4:
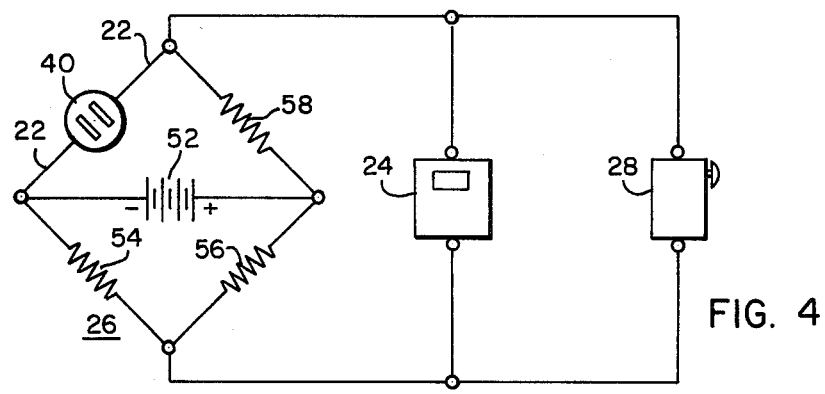
FIG. 4 shows an electrical schematic of the caustic detector circuit.

FIG. 4 shows an electrical schematic for this invention illustrating electrodes 40 and their connection with multi-channel recorder 24, suitable alarm system such as audio-visual 28, and wheatstone bridge 26. Wheatstone bridge 26 is of conventional design and has included therein: a direct current source 52, and suitable resistors 54, 56, and 58 which provide a means for measuring electrical conductivity between electrodes 40 with the measured conductivity providing an indication of the quantity of molten caustic which has accumulated therebetween.

It will now be apparent that an improved steam turbine caustic detector has been provided which will give an earlier alarm than was heretofore possible while allowing the avoidance of many forced outages previously caused by caustic deterioration of crossover conduit expansion joints and other vulnerable regions of the steam turbine system. Although this invention has been shown embodied in only one location, by utilizing a multi-channel recorder 24 and additional electrical probes suitably disposed throughout the turbine, the presence of molten caustic substances anywhere in the turbine can be closely monitored resulting in reduced caustic corrosion cracking. Although certain preferred materials such as nickel has been described for the purposes of illustration, other suitable materials with like properties can be used in their place. While the invention has been illustrated by only one embodiment, it is to be understood that in the broadest aspects of the invention certain changes may be made by the omission of unwanted parts, by the addition of parts, or in the substitution of equivalents without departing from the broadest aspects of the invention.

I claim:

1. A steam turbine system caustic detector comprising:
   a steam turbine having a plurality of separate housings;
   a first conduit for carrying steam between said turbine housings;
   a second conduit which cooperates with and functions as an expansion joint for said first conduit, said second conduit having a wall of circumferentially disposed, axially alternating inward and outward protruding convolutions;
   a pair of electrical probes each of which have a first and second end, said first ends being insertable through an outward protruding convolution at the bottom of said second conduit, said first ends being suitably separated;
   means for applying an electrical potential across said electrical probes; and
   means for measuring current flow through said electrical probes whereby said current measuring means will indicate a current when a caustic of suitable electrical conductivity collects in said outward protruding convolution in sufficient quantity to electrically connect said probes' first ends.

2. The steam turbine system caustic detector of claim 1, said pair of electrical probes comprising:
   two insulated electrical conductors whose first ends form electrodes which are spatially separated and which each have a surface that slopes away from the opposite electrode in such a manner as to form a trough therebetween.

3. The steam turbine system caustic detector of claim 1, further comprising:
   a baffle for shielding said probe's first ends from direct impingement by steam and steam-born material, said baffle being disposed upstream of said first ends.

4. The steam turbine system caustic detector of claim 1, further comprising:
   means for providing an alarm indication when said current exceeds a predetermined level.

5. The steam turbine system caustic detector of claim 1, further comprising:
   a drain, blowdown scheme attached to said second conduit whereby molten caustic, accumulated in said second conduit, can be removed therefrom.

* * * * *